United States Patent
Reilly, III

(10) Patent No.: US 11,147,835 B1
(45) Date of Patent: Oct. 19, 2021

(54) NUTRITIONAL SUPPLEMENT

(71) Applicant: Frank Kelly Reilly, III, West Chester, PA (US)

(72) Inventor: Frank Kelly Reilly, III, West Chester, PA (US)

(*) Notice: Subject to any disclaimer, the term of this patent is extended or adjusted under 35 U.S.C. 154(b) by 0 days.

(21) Appl. No.: 16/997,993

(22) Filed: Aug. 20, 2020

(51) Int. Cl.
| | | |
|---|---|---|
| *A61K 33/30* | (2006.01) | |
| *A61K 45/06* | (2006.01) | |
| *A61K 31/375* | (2006.01) | |
| *A61K 31/355* | (2006.01) | |
| *A61K 31/4415* | (2006.01) | |
| *A61K 47/44* | (2017.01) | |
| *A23L 33/15* | (2016.01) | |
| *A23L 33/16* | (2016.01) | |
| *A23L 33/105* | (2016.01) | |
| *A61K 31/05* | (2006.01) | |

(52) U.S. Cl.
CPC ............ *A61K 33/30* (2013.01); *A23L 33/105* (2016.08); *A23L 33/15* (2016.08); *A23L 33/16* (2016.08); *A61K 31/05* (2013.01); *A61K 31/355* (2013.01); *A61K 31/375* (2013.01); *A61K 31/4415* (2013.01); *A61K 45/06* (2013.01); *A61K 47/44* (2013.01); *A23V 2002/00* (2013.01)

(58) Field of Classification Search
CPC ...... A61K 33/30; A61K 31/05; A61K 31/355; A61K 31/375; A61K 31/4415; A61K 45/06; A61K 47/44; A23L 33/105; A23L 33/16; A23L 33/15; A23V 2002/00
See application file for complete search history.

(56) References Cited

U.S. PATENT DOCUMENTS

| | | | |
|---|---|---|---|
| 5,221,668 A | 6/1993 | Henningfield et al. | |
| 9,463,212 B2 | 10/2016 | Willimann | |
| 9,855,311 B2 | 1/2018 | Singhal | |
| 10,064,905 B1* | 9/2018 | Jenn ....................... | A23L 33/105 |
| 10,201,553 B1 | 2/2019 | Steinberg et al. | |
| 2003/0185918 A1 | 10/2003 | Rosenbloom | |
| 2006/0110477 A1 | 5/2006 | McCleary | |
| 2006/0110478 A1* | 5/2006 | McCleary .............. | A61K 36/85 |
| | | | 424/757 |
| 2008/0031980 A1* | 2/2008 | Rodriguez .......... | A61K 36/9066 |
| | | | 424/773 |
| 2009/0118373 A1 | 5/2009 | Tripp et al. | |
| 2013/0266672 A1 | 10/2013 | Bombardelli et al. | |
| 2015/0190450 A1 | 7/2015 | Chang | |
| 2016/0206673 A1* | 7/2016 | Miller ..................... | A61K 36/23 |
| 2017/0112178 A1 | 4/2017 | Perrin | |

FOREIGN PATENT DOCUMENTS

| | | |
|---|---|---|
| CN | 101444266 | 6/2011 |
| CN | 104296425 | 1/2015 |
| CN | 105211607 | 1/2015 |
| CN | 104336330 | 2/2015 |
| CN | 10636058 | 1/2016 |
| CN | 106071406 | 11/2016 |
| CN | 106107229 | 11/2016 |
| CN | 106173391 | 12/2016 |
| CN | 106259090 | 1/2017 |
| CN | 106259096 | 1/2017 |
| CN | 106259097 | 1/2017 |
| CN | 106387394 | 2/2017 |
| CN | 106508745 | 3/2017 |
| CN | 106508787 | 3/2017 |
| CN | 104286585 | 9/2017 |
| KR | 19960003738 | 2/1996 |
| WO | WO99/51250 | 10/1999 |
| WO | WO2005/095375 | 10/2005 |
| WO | WO2009/010992 | 1/2009 |
| WO | WO2018067604 | 4/2018 |
| WO | WO2019/074617 | 4/2019 |

OTHER PUBLICATIONS

Euromedica, "Hemp oil +Curcumin", Jul. 2019. (Year: 2019).*
Butter, "Want better Sex? There's an oil For That", Jun. 5, 2015, retrieved from https://www.hippiebutter.com/news/want-better-sex-theres-an-oil-for-that on Oct. 14, 2020. (Year: 2015).*
MSKC, "Sophora Flavescens", Feb. 12, 2014, retrieved from https://www.mskcc.org/cancer-care/integrative-medicine/herbs/sophora-flavescens on Oct. 13, 2020. (Year: 2014).*
Brilliant C Plus. Oct. 23, 2019.

* cited by examiner

Primary Examiner — Jianfeng Song
(74) Attorney, Agent, or Firm — Joseph E. Maenner; Petock & Petock LLC

(57) ABSTRACT

A nutritional supplement provides Vitamin E; *Sophora Flavescens* extract; zinc; and at least two ingredients selected from the group consisting of hemp grapeseed extract, hemp curcumin, hemp boswellia, hemp black pepper, hemp magnolia, hemp ginger, hemp oregano leaf, hemp orange peel, hemp methyl sulfano methane (MSM), hemp poplar, hemp chia, hemp meadow sweet, hemp clove powder, hemp cinnamon, and hemp basil (excluding hay basil and hay basil extract). The supplement can be used to reduce joint inflammation, reduce stiffness, reduce lameness, improve flexion, and improve amount of movement and mobility by supporting joint health.

1 Claim, No Drawings

NUTRITIONAL SUPPLEMENT

BACKGROUND OF THE INVENTION

Field of the Invention

The present invention relates to a nutritional supplement to aid in reducing inflammation.

Prior Art

Nutritional supplements are well known in the equine industry for relieving joint inflammation.

It would be beneficial to provide a nutritional supplement containing only natural ingredients.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a nutritional supplement comprising Vitamin E; *Sophora Flavescens* extract; zinc; and at least two ingredients selected from the group consisting of hemp grapeseed extract, hemp curcumin, hemp boswellia, hemp black pepper, hemp magnolia, hemp ginger, hemp oregano leaf, hemp orange peel, hemp methyl sulfano methane (MSM), hemp poplar, hemp chia, hemp meadow sweet, hemp clove powder, hemp cinnamon, and hemp basil (excluding hay basil and hay basil extract). The supplement can be used to reduce joint inflammation.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Unless explicitly stated otherwise, each numerical value and range should be interpreted as being approximate as if the word "about" or "approximately" preceded the value of the value or range.

The present invention provides a nutritional supplement. While the invention is directed to use in an equine environment, those skilled in the art will recognize that the inventive supplement can be used on other animals as well. The supplement can be an oral supplement in the form of a powder, liquid, tablet, capsule, or a patch or topical ointment. The supplement can be used to reduce inflammation of joints, connective tissue, and musculoskeletal systems (including tendons/ligaments), resulting in increased mobility and comfort. The supplement can also be used to prevent and treat diseases of the joint, connective tissue, and musculoskeletal system, post surgery, fractures, etc.

In a first exemplary embodiment, the supplement includes *Sophora Flavescens* extract, zinc, and vitamin C. In an exemplary embodiment, the supplement includes between about 100 mg and about 5 grams of zinc in various forms, including, but not limited to, sulfate, picolinate, chelate, raw (plant based zinc), gluconate, oratate, acetate, and oxide); between about 100 mg and about 5 grams of *sophora flavecens* extract in a ratio of dry herb weight to extract weight of between about 2:1 and about 20:1., and can be alcohol or non-alcohol derived extract, and can be in powder, liquid, solid, crystalline form; and between about 100 mg and about 5 grams of Vitamin C.

Optionally, the supplement can also include any one or more of hemp and hemp cannabinoids (CBA), including cannabidiol (CBD), Cannabigerol (CBG), hemp seed oil, full spectrum hemp oil, and hemp protein powder.

In an exemplary embodiment, the supplement includes the following ingredients in the respective percentages, by weight:

| Ingredient | Percentage |
| --- | --- |
| Vitamin E | 12% |
| Grape Seed Extract | 2% |
| Boswellia Extract | 1% |
| Micronized Resveratrol | 1% |
| Vitamin B6 | 0.6% |
| Black Pepper Powder | 1% |
| Orange Peel Powder | 1% |
| Magnolia Powder | 6% |
| Curcumin Powder | 2.7% |
| Poplar Powder | 2% |
| Willow Bark Powder | 2% |
| MSM | 6% |
| Whole Chia Seeds | 13% |
| Zinc Sulfate | 7.5% |
| Vitamin C | 7.5% |
| Pine Powder | 10% |
| Sophora Flavescens Extract | 0.5% |
| Hemp Protein Powder (Hemp Seed Protein Powder) | 4% |
| Hemp Seed Oil | 0.5% |
| Cloves Powder | 0.2% |

| | |
|---|---|
| Cinnamon Powder | 1% |
| Common Basil Powder | 0.5% |
| Meadow Sweet Powder | 7% |
| Total: | 88.8% |

The supplement can also include a remainder of any of the following, typically in total weight percentages of less than or equal to 11.2 percent: hemp grapeseed extract, hemp curcumin, hemp boswellia, hemp black pepper, hemp magnolia, hemp ginger, hemp oregano leaf, hemp orange peel, hemp methyl sulfano methane (MSM), hemp poplar, hemp chia, hemp meadow sweet, hemp clove powder, hemp cinnamon, hemp basil (excluding hay basil, hay basil extract, holy basil, and holy basil extract), hemp olive leaf (excluding olive leaf extract).

In an exemplary embodiment, the supplement can also include a remainder of any of the following, typically in total weight percentages of less than or equal to 11.2 percent: Vitamin C, *Sophora Flavescens* extract, zinc, and at least two of grape seed extract, pine, magnolia, poplar, meadowsweet, basil, orange peel, and cloves, along with hemp seed oil and/or hemp protein powder.

Optionally, the supplement can also include a pharmaceutical, such as, for example, NSAIDS, nitric oxide inhibitors, steroids, antimicrobials (bacteria, fungus, virus, parasitic), hormones, anti-inflammatory—NSAIDS—cyclo-oxygenase inhibitors, anti-inflammatory—lipo-oxygenase inhibitors, acetaminophen, anti-inflammatory—glucocorticoids, NOS Inhibitors (nitric oxide), opioids, anabolic steroids, tranquilizers/anti-depressants, antihistamines, central & peripheral nervous system anesthetics, antiparasites, glycosupplements (chondroitin, glucosamine), hyaluronic acid, DMSO—dimethyl sulfoxide, immune modulation/mediation medications, collagen, hormones (including but not limited to thyroid, melatonin, reproductive, pituitary/brain), autoimmune pharmaceuticals, and vitamins/minerals/amino acids/Omega 3 fatty acids.

In an exemplary embodiment, the supplement has an absence of gluten, genetically modified organisms (GMOs), melamine, pesticides, and lead.

It will be further understood that various changes in the details, materials, and arrangements of the parts which have been described and illustrated in order to explain the nature of this invention may be made by those skilled in the art without departing from the scope of the invention as expressed in the following claims.

I claim:
1. A nutritional supplement consisting of:
   12% by weight Vitamin E;
   0.5% by weight *Sophora Flavescens* extract;
   7.5% by weight zinc sulfate;
   less than or equal to 11.2% by weight of at least two ingredients selected from the group consisting of:
      hemp grapeseed extract,
      hemp Boswellia,
      hemp black pepper,
      hemp magnolia,
      hemp ginger,
      hemp oregano leaf,
      hemp methyl sulfano methane,
      hemp poplar,
      hemp chia,
      hemp meadowsweet,
      hemp clove powder,
      hemp cinnamon,
      hemp basil and
      hemp olive leaf; and
   a remainder of at least one ingredient selected from the group consisting of:
      grape seed extract,
      Boswellia extract,
      Micronized Resveratrol,
      Vitamin B6,
      Black pepper powder,
      Magnolia powder,
      Poplar powder,
      Willow bark powder,
      methyl sulfano methane,
      whole chia seeds,
      Vitamin C,
      Pine powder,
      Hemp protein powder,
      Hemp seed oil,
      Cloves powder,
      Cinnamon powder,
      common basil powder,
      Curcumin,
      Orange peel and
      Meadow seed powder.

* * * * *